(12) United States Patent
Jaax et al.

(10) Patent No.: US 8,315,707 B2
(45) Date of Patent: Nov. 20, 2012

(54) SYSTEM AND METHOD FOR AVOIDING, REVERSING, AND MANAGING NEUROLOGICAL ACCOMMODATION TO ELECTRICAL STIMULATION

(75) Inventors: Kristen Jaax, Santa Clara, CA (US); Andrew DiGiore, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/423,245

(22) Filed: Mar. 18, 2012

(65) Prior Publication Data
US 2012/0179222 A1    Jul. 12, 2012

Related U.S. Application Data

(63) Continuation of application No. 12/509,340, filed on Jul. 24, 2009, now Pat. No. 8,155,750.

(60) Provisional application No. 61/083,490, filed on Jul. 24, 2008.

(51) Int. Cl.
*A61N 1/00* (2006.01)
(52) U.S. Cl. .......................................... 607/59
(58) Field of Classification Search .................. 607/59
See application file for complete search history.

(56) References Cited

U.S. PATENT DOCUMENTS

| | | | |
|---|---|---|---|
| 4,759,368 A | 7/1988 | Spanton et al. | |
| 5,215,086 A | 6/1993 | Terry, Jr. et al. | |
| 5,263,480 A | 11/1993 | Wernicke et al. | |
| 5,335,657 A | 8/1994 | Terry, Jr. et al. | |
| 5,397,338 A | 3/1995 | Grey et al. | |
| 6,167,304 A | 12/2000 | Loos | |
| 6,516,227 B1 | 2/2003 | Meadows et al. | |
| 6,594,523 B1 | 7/2003 | Levine | |
| 6,606,516 B2 | 8/2003 | Levine | |

(Continued)

FOREIGN PATENT DOCUMENTS

EP    1201266 A1    2/2002

(Continued)

OTHER PUBLICATIONS

Bendetti, Fabrizio MD, et al. Control of Postoperative Pain by Transcutaneous Electrical Nerve Stimulation After Thoracic Operations. Ann. Thorac. Surg. 1997; 63: 773-776 (4 pages).

(Continued)

*Primary Examiner* — George Manuel
*Assistant Examiner* — Robert N Wieland
(74) *Attorney, Agent, or Firm* — Vista IP Law Group LLP

(57) ABSTRACT

A method of operating a neurostimulation device comprises varying a first stimulation parameter under user control while fixing a second stimulation parameter, generating a plurality of stimulation parameter sets from the varied first stimulation parameter and the fixed second stimulation parameter, outputting a pulsed electrical waveform from the neurostimulation device between electrodes in accordance with the stimulation parameter sets, such that a therapeutic effect is achieved while allowing neural tissue to undergo neurological accommodation, changing the second stimulation parameter, varying the first stimulation parameter under user control while fixing the second changed stimulation parameter, generating another plurality of stimulation parameter sets from the varied first stimulation parameter and the fixed changed second stimulation parameter, and outputting the pulsed electrical waveform from the neurostimulation device between the electrodes in accordance with the other stimulation parameter sets to maintain the therapeutic effect while the neural tissue is neurologically accommodated.

30 Claims, 10 Drawing Sheets

U.S. PATENT DOCUMENTS

| | | |
|---|---|---|
| 6,895,280 B2 | 5/2005 | Meadows et al. |
| 6,993,384 B2 | 1/2006 | Bradley et al. |
| 7,181,286 B2 | 2/2007 | Sieracki et al. |
| 7,295,876 B1 | 11/2007 | Erickson |
| 7,539,538 B2 | 5/2009 | Parramon et al. |
| 7,853,329 B2 * | 12/2010 | DiLorenzo ............ 607/45 |
| 2002/0022866 A1 | 2/2002 | Borkan |
| 2002/0055762 A1 | 5/2002 | Gliner |
| 2002/0151935 A1 | 10/2002 | Levine |
| 2003/0135248 A1 | 7/2003 | Stypulkowski |
| 2003/0139781 A1 | 7/2003 | Bradley et al. |
| 2003/0195579 A1 | 10/2003 | Bradley et al. |
| 2004/0034394 A1 | 2/2004 | Woods et al. |
| 2004/0098065 A1 | 5/2004 | Hagglof et al. |
| 2004/0143302 A1 | 7/2004 | Sieracki et al. |
| 2004/0249422 A1 | 12/2004 | Gliner et al. |
| 2005/0004622 A1 | 1/2005 | Cullen et al. |
| 2005/0267546 A1 | 12/2005 | Parramon et al. |
| 2006/0089683 A1 | 4/2006 | Hagglof et al. |
| 2006/0116737 A1 | 6/2006 | Libbus |
| 2006/0259099 A1 | 11/2006 | Goetz et al. |
| 2007/0073356 A1 | 3/2007 | Rooney et al. |
| 2007/0073357 A1 | 3/2007 | Rooney et al. |
| 2007/0123956 A1 | 5/2007 | Sieracki et al. |
| 2007/0150034 A1 | 6/2007 | Rooney et al. |
| 2007/0203521 A1 | 8/2007 | Dobak et al. |
| 2007/0255346 A1 | 11/2007 | Rondoni et al. |
| 2007/0265664 A1 | 11/2007 | Gerber et al. |
| 2007/0265681 A1 | 11/2007 | Gerber et al. |
| 2008/0033511 A1 | 2/2008 | Dobak |
| 2008/0065183 A1 * | 3/2008 | Whitehurst et al. ........ 607/116 |
| 2008/0243204 A1 * | 10/2008 | Uthman et al. ............ 607/45 |
| 2009/0118777 A1 | 5/2009 | Iki et al. |

FOREIGN PATENT DOCUMENTS

| | | |
|---|---|---|
| WO | WO 2004/041352 | 5/2004 |
| WO | WO 2005/007236 | 1/2005 |
| WO | WO 2005/068017 | 7/2005 |
| WO | WO 2007/127455 | 11/2007 |
| WO | WO 2007/127460 | 11/2007 |
| WO | WO 2007/130169 A1 | 11/2007 |
| WO | WO 2007/146287 A2 | 12/2007 |
| WO | WO 2008/052085 A1 | 5/2008 |

OTHER PUBLICATIONS

PCT International Search Report for PCT/US2009/051755, Applicant: Boston Scientific Neuromodulation Corporation, Form PCT/ISA/210 and 220, dated Oct. 22, 2009 (8 pages).

PCT Written Opinion of the International Search Authority for PCT/US2009/051755, Applicant: Boston Scientific Neuromodulation Corporation, Form PCT/ISA/237, dated Oct. 22, 2009 (7 pages).

PCT International Search Report for PCT/US2009/051755, Applicant: Boston Scientific Neuromodulation Corporation, Form PCT/ISA/210 and 220, dated Dec. 22, 2009 (8 pages).

PCT Written Opinion of the International Search Authority for PCT/US2009/051755, Applicant: Boston Scientific Neuromodulation Corporation, Form PCT/ISA/237, dated Dec. 22, 2009 (7 pages).

PCT International Preliminary Report on Patentability (Chapter I of the Patent Cooperation Treaty) for PCT/US2009/051755, Applicant: Boston Scientific Neuromodulation Corporation, Form PCT/IB/326 and 373, dated Feb. 3, 2011 (9pages).

* cited by examiner

SYSTEM AND METHOD FOR AVOIDING, REVERSING, AND MANAGING NEUROLOGICAL ACCOMMODATION TO ELECTRICAL STIMULATION

RELATED APPLICATION

The present application is a continuation of U.S. patent application Ser. No. 12/509,340, filed Jul. 24, 2009, which claims the benefit under 35 U.S.C. §119 to U.S. provisional patent application Ser. No. 61/083,490, filed Jul. 24, 2008. The foregoing applications are hereby incorporated by reference in the present application in their entireties.

FIELD OF THE INVENTION

The present invention relates to tissue stimulation systems, and more particularly, to a system and method for programming an implantable tissue stimulator.

BACKGROUND OF THE INVENTION

Spinal cord stimulation (SCS) is a well-accepted clinical method for reducing pain in certain populations of patients. Spinal cord stimulator and other implantable tissue stimulator systems come in two general types: radio-frequency (RF)-controlled and fully implanted.

The type commonly referred to as an "RF" system includes an external RF transmitter inductively coupled via an electromagnetic link to an implanted receiver-stimulator connected to one or more leads with one or more electrodes for stimulating tissue. The power source, e.g., a battery, for powering the implanted receiver, as well as control circuitry to command the receiver-stimulator, is contained in the RF transmitter—a hand-held sized device typically worn on the patient's belt or carried in a pocket. Data/power signals are transcutaneously coupled from a cable-connected transmission coil connected to the RF transmitter and placed over the implanted receiver-stimulator. The implanted receiver-stimulator receives the signal and generates the stimulation.

In contrast, the fully implanted type of stimulating system contains the control circuitry, as well as a power supply, e.g., a battery, all within an implantable pulse generator (IPG), so that once programmed and turned on, the IPG can operate independently of external hardware. The IPG is turned on and off and programmed to generate the desired stimulation pulses from an external portable programming device using transcutaneous electromagnetic or RF links.

In both the RF-controlled or fully implanted systems, the electrode leads are implanted in the epidural space, or alternatively near the dura of the spinal cord. Individual wires within one or more electrode leads connect with each electrode on the lead. The electrode leads exit the spinal column and, when necessary, attach to one or more electrode lead extensions. The electrode leads or extensions are typically tunneled within the subcutaneous tissue along the torso of the patient to a subcutaneous pocket where the receiver-stimulator or IPG is implanted. The RF transmitter or IPG can then be operated to generate electrical pulses that are delivered, through the electrodes, to the targeted tissue, and in particular, the dorsal column fibers and dorsal root fibers within the spinal cord. The stimulation creates the sensation known as paresthesia, which can be characterized as an alternative sensation that replaces the pain signals sensed by the patient.

Individual electrode contacts (the "electrodes") are arranged in a desired pattern and spacing in order to create an electrode array. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied in SCS include electrical pulse parameters, which may define the pulse amplitude (measured in milliamps or volts depending on whether constant current or constant voltage is supplied to the electrodes), pulse duration (measured in microseconds), pulse rate (measured in pulses per second), pulse shape, and burst rate (measured as the stimulation on duration per unit time). Each electrode combination, along with the electrical pulse parameters, can be referred to as a "stimulation parameter set."

With some SCS systems, and in particular, SCS systems with independently controlled current or voltage sources, the distribution of the current to the electrodes (including the case of the receiver-stimulator or IPG, which may act as an electrode) may be varied such that the current is supplied via numerous different electrode configurations. In different configurations, the electrodes may provide current (or voltage) in different relative percentages of positive and negative current (or voltage) to create different electrode configuration, and in particular, fractionalized electrode configurations.

As briefly discussed above, an external control device, such as an RF controller or portable programming device, can be used to instruct the receiver-stimulator or IPG to generate electrical stimulation pulses in accordance with the selected stimulation parameters. Typically, the stimulation parameters programmed into the external device, itself, can be adjusted by manipulating controls on the external device itself to modify the electrical stimulation provided by the SCS system to the patient. However, the number of electrodes available, combined with the ability to generate a variety of complex stimulation pulses, presents a huge selection of stimulation parameter sets to the clinician or patient.

To facilitate such selection, the clinician generally programs the external control device, and if applicable the IPG, through a computerized programming system. This programming system can be a self-contained hardware/software system, or can be defined predominantly by software running on a standard personal computer (PC). The PC or custom hardware may actively control the characteristics of the electrical stimulation generated by the receiver-stimulator or IPG to allow the optimum stimulation parameters to be determined based on patient feedback and to subsequently program the RF transmitter or portable programming device with the optimum stimulation parameters. The computerized programming system may be operated by a clinician attending the patient in several scenarios.

For example, in order to achieve an effective result from SCS, the lead or leads must be placed in a location, such that the electrical stimulation will cause paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the RF transmitter or IPG to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the IPG, with a set of stimulation parameters that best addresses the painful site. Thus, the navigation session may be used to pinpoint the stimulation region or areas correlating to the pain. Such programming ability is particularly advantageous after implantation should the leads gradually or unexpectedly move, thereby relocating the paresthesia away from the pain site. By reprogramming the external control device, the stimulation region can often be moved back to the effective pain site without having to reoperate on the patient in order to reposition the lead and its electrode array.

Even when using a computerized programming system, programming or reprogramming the external control device or IPG may be a difficult task. Oftentimes, a clinician may identify a stimulation parameter set where a patient is obtaining great paresthesia, but when the clinician subsequently returns to this stimulation parameter set, even within the same programming session, the patient may no longer receive the same paresthesia. In some cases, the patient may not feel any paresthesia at all when the clinician returns to this stimulation parameter set.

Candidate reasons for the change in paresthesia over time are neurologic phenomena, such as accommodation, adaptation, and habituation, which entail a diminished neural response over time when there exists continuous input (in this case, electrical stimulation) due to cellular and synaptic mechanisms. For the purposes of this specification, we will use the term "accommodation" to generally refer to any mechanism that diminishes neural response due to continuous input. Currently-used methods to avoid accommodation include a 1-hour rest interval to avoid accommodation of nerve fibers (see Benedetti, Fabrizio M D, et al; Control of Postoperative Pain by Transcutaneous Electrical Nerve Stimulation After Thoracic Operations. Ann Thorac Surg 1997; 63: 773-776). However, this is an unrealistic solution as it would more than double the time needed for a programming session. Increased programming time leads to higher workloads for the clinicians and increased costs. Furthermore, once neurological accommodation has occurred, there are currently no techniques to reverse or otherwise manage the accommodation.

There, thus, remains a need for an improved method and system that avoids, reverses, or otherwise manages neurological accommodation during the programming of neurostimulation devices.

SUMMARY OF THE INVENTION

The present inventions are directed to methods and programmers for avoiding, reversing, or otherwise managing neurological accommodation;

In accordance with a first aspect of the present inventions, a method of programming a neurostimulation device is provided. The method comprises varying a first stimulation parameter (e.g., an electrode combination or a fractionalized electrode combination) under user control. If the first stimulation parameter is a fractionalized electrode combination, it can be varied by gradually shifting current between anodic electrodes or gradually shifting current between cathodic electrodes.

The method further comprises automatically varying a second stimulation parameter as the first stimulation parameter is varied under user control. In one method, the second stimulation parameter is pseudo-randomly or randomly varied. The second stimulation parameter may be, e.g., an electrode combination or an electrical pulse parameter, such as a pulse amplitude, pulse width, a pulse shape, or burst rate. If the second stimulation parameter is a pulse amplitude, it can be varied by both increasing and decreasing the amplitude of the pulses. If both the pulse amplitude and pulse width are varied, they can be inversely varied relative to each other, e.g., such that the pulsed electrical waveform is maintained within a predetermined range of a strength-duration curve for the neural tissue.

The method further comprises generating a plurality of stimulation parameter sets from the varied first and second stimulation parameters, and outputting a pulsed electrical waveform from the neurostimulation device between a plurality of electrodes in accordance with the plurality of stimulation parameter sets, such that neural tissue (e.g., spinal cord tissue) is stimulated without undergoing neurological accommodation that would otherwise occur if the second stimulation parameter were not varied. The method further comprises programming the neurostimulation device with a new set of stimulation parameters based on a result of the neural tissue stimulation.

In accordance with a second aspect of the present inventions, a programmer for a neurostimulation device is provided. The programmer comprises a user interface capable of receiving an input from a user, and a processor configured for varying a first stimulation parameter in response to the user input, automatically varying a second stimulation parameter as the first stimulation parameter is varied in response to the user input, generating a plurality of stimulation parameter sets from the varied first and second stimulation parameters, and programming the neurostimulation device with a new set of stimulation parameters.

The processor may vary the first and second stimulation parameters in the manner described above. The user interface may comprise an actuator, in which case, the processor may be configured for generating the plurality of stimulation parameter sets in response to actuation of the actuator. The programmer further comprises output circuitry configured for transmitting the plurality of stimulation parameter sets and the new stimulation parameter set to the neurostimulation device. The output circuitry may be telemetry circuitry configured for wirelessly transmitting the plurality of stimulation parameter sets and the new stimulation parameter set to the neurostimulation device.

In accordance with a third aspect of the present inventions, a method of operating a neurostimulation device is provided. The method comprises outputting a pulsed electrical waveform from the neurostimulation device between a plurality of electrodes while at least one of the electrodes has a first polarity, thereby stimulating neural tissue adjacent the at least one electrode. In one method, the pulsed electrical waveform is output between the electrodes in accordance with a set of stimulation parameters, in which case, the method further comprises varying one or more of the stimulation parameters under user control as the pulsed electrical waveform is output between the electrodes while the electrode(s) has the first polarity.

The method further comprises allowing the neural tissue to undergo neurological accommodation in response to the electrical energy output between the electrodes, switching the electrode(s) from the first polarity to a second polarity (which may be automatically initiated), and outputting the pulsed electrical waveform from the neurostimulation device between the electrodes while the electrode(s) has the second polarity, thereby hyperpolarizing the neural tissue to reverse the neurological accommodation.

The method further comprises switching the electrode(s) from the second polarity to the first polarity (which may be automatically initiated), and outputting the pulsed electrical waveform from the neurostimulation device between the electrodes while the electrode(s) has the first polarity, thereby stimulating the previously hyperpolarized neural tissue. In one method, each of the electrode(s) is a cathode when in the first polarity, and is an anode when in the second polarity. In another method, the pulsed electrical waveform output has a first amplitude when the electrode(s) has the first polarity, and the pulsed electrical waveform output has a second lesser amplitude when the electrode(s) has the second polarity. For example, the second amplitude may be equal to a third or less of the first amplitude. The method may optionally comprise programming the neurostimulation device with a new set of stimulation parameters based on a result of the neural tissue stimulation.

In accordance with a fourth aspect of the present invention another method of operating a neurostimulation device is provided. The method comprises varying a first stimulation parameter (e.g., an electrode combination or a fractionalized electrode combination) under user control while fixing a second stimulation parameter (e.g., a pulse rate or pulse width). If the first stimulation parameter is a fractionalized electrode combination, it can be varied by gradually shifting current between anodic electrodes or gradually shifting current between cathodic electrodes.

The method further comprises generating a plurality of stimulation parameter sets from the varied first stimulation parameter and the fixed second stimulation parameter, and outputting a pulsed electrical waveform from the neurostimulation device between a plurality of electrodes in accordance with the plurality of stimulation parameter sets, such that a therapeutic effect (e.g., pain relief) is achieved while allowing neural tissue (e.g., spinal cord tissue) to undergo neurological accommodation.

The method further comprises changing the second stimulation parameter (which may be automatically initiated), and varying the first stimulation parameter under user control while fixing the second changed stimulation parameter.

In one method, the second stimulation parameter is changed in accordance with a predetermined curve. In this case, the predetermined curve may be based on data collected from patients that have undergone neurological accommodation.

In another method, a reference set of stimulation parameters is generated from a first reference stimulation parameter of the same type as the first stimulation parameter, and a second stimulation parameter of the same type as the second stimulation parameter. Prior to allowing the neural tissue to undergo neurological accommodation, the pulsed electrical waveform is outputted from the neurostimulation device between the electrodes in accordance with the reference stimulation parameter set, thereby stimulating the neural tissue to provide a reference therapeutic effect. After allowing the neural tissue to undergo neurological accommodation, the pulsed electrical waveform is outputted from the neurostimulation device between the electrodes in accordance with the reference stimulation parameter set, thereby providing an effect different from the reference therapeutic effect, and varying the second reference stimulation parameter until the effect matches the reference therapeutic effect. The varied second reference stimulation parameter is then used as the changed second stimulation parameter.

The method further comprises generating another plurality of stimulation parameter sets from the varied first stimulation parameter and the fixed changed second stimulation parameter, outputting the pulsed electrical waveform from the neurostimulation device between the plurality of electrodes in accordance with the other plurality of stimulation parameter sets to maintain the therapeutic effect while the neural tissue is neurologically accommodated. The method may optionally comprise programming the neurostimulation device with a new set of stimulation parameters based on a result of the therapeutic effect.

In accordance with a fifth aspect of the present invention, still another method of operating a neurostimulation device is provided. The method comprises outputting a pulsed electrical waveform from the neurostimulation device between a plurality of electrodes in accordance with a specified pulse amplitude and a specified pulse width.

The method further comprises maintaining the pulsed electrical waveform between a first strength-duration curve for relatively large fibers of neural tissue (e.g., spinal cord tissue) and a second strength-duration curve for relatively small fibers of the neural tissue, whereby the relatively large fibers are stimulated and the relatively small fibers are not stimulated.

The method further comprises allowing the relatively large fibers of the neural tissue to neurologically accommodation when the pulsed electrical waveform is between the first and second strength-duration curves, and increasing one or both of the specified amplitude and the specified pulse width, such that the pulsed electrical waveform is on or above the second strength-duration curve, whereby the relatively small fibers are stimulated.

In one method, the specified amplitude and the specified pulse width are automatically increased. In another method, one or both of the specified amplitude and the specified pulse width is increased at a predetermined period of time after the pulsed electrical waveform is initially output by the neurostimulation device. The method may optionally comprise programming the neurostimulation device with a new set of stimulation parameters based on a result of the neural stimulation.

The method may further comprise varying a stimulation parameter (e.g., an electrode combination or a fractionalized electrode combination) under user control. If the stimulation parameter is a fractionalized electrode combination, it can be varied by gradually shifting current between the anodic electrodes or gradually shifting current between the cathodic electrodes.

In accordance with a sixth aspect of the present invention, yet another method of programming a neurostimulation device is provided. The method comprises initially outputting a pulsed electrical waveform from the neurostimulation device between a plurality of electrodes, such that neural tissue (e.g., spinal cord tissue) of a patient is stimulated and undergoes neurological accommodation. In one method, the pulsed electrical waveform is initially output with the highest pulse amplitude tolerable for the patient. The method further comprises decreasing a pulse amplitude of the pulsed electrical waveform, and generating a plurality of stimulation parameter sets having the decreased amplitude.

The method further comprises outputting the pulsed electrical waveform with the decreased pulse amplitude in accordance with the stimulation parameter sets, such that the neural tissue is stimulated and remains neurologically accommodated, and programming the neurostimulation device with a new set of stimulation parameters based on a result of the neural tissue stimulation.

The method may further comprise varying a stimulation parameter (e.g., an electrode combination or a fractionalized electrode combination) under user control, in which case, the plurality of stimulation parameter sets are generated from the varied stimulation parameter. If the stimulation parameter is a fractionalized electrode combination, it can be varied by gradually shifting current between anodic ones of the electrodes or gradually shifting current between cathodic ones of the electrodes.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

At the outset, it is noted that the present invention may be used with an implantable pulse generator (IPG), radio frequency (RF) transmitter, or similar electrical stimulator, that may be used as a component of numerous different types of stimulation systems. The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
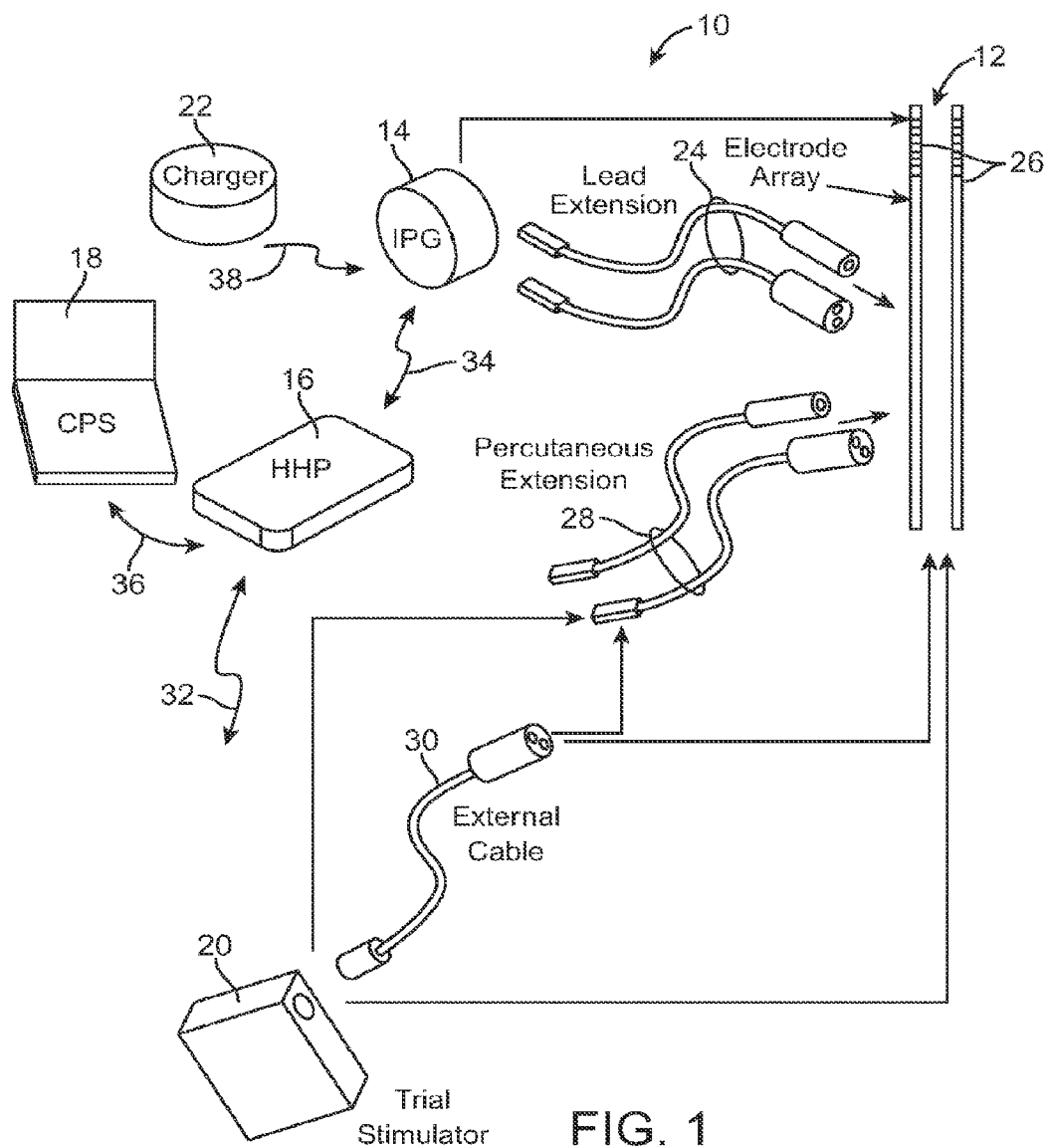
FIG. 1 is perspective view of one embodiment of a SCS system arranged in accordance with the present inventions.

Turning first to FIG. 1, an exemplary SCS system 10 generally includes one or more (in this case, two) implantable stimulation leads 12, an implantable pulse generator (IPG) 14, an external remote controller RC 16, a clinician's programmer (CP) 18, an external trial stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as the IPG 14, also delivers electrical stimulation energy in the form of a pulse electrical waveform to the electrode array 26 in accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
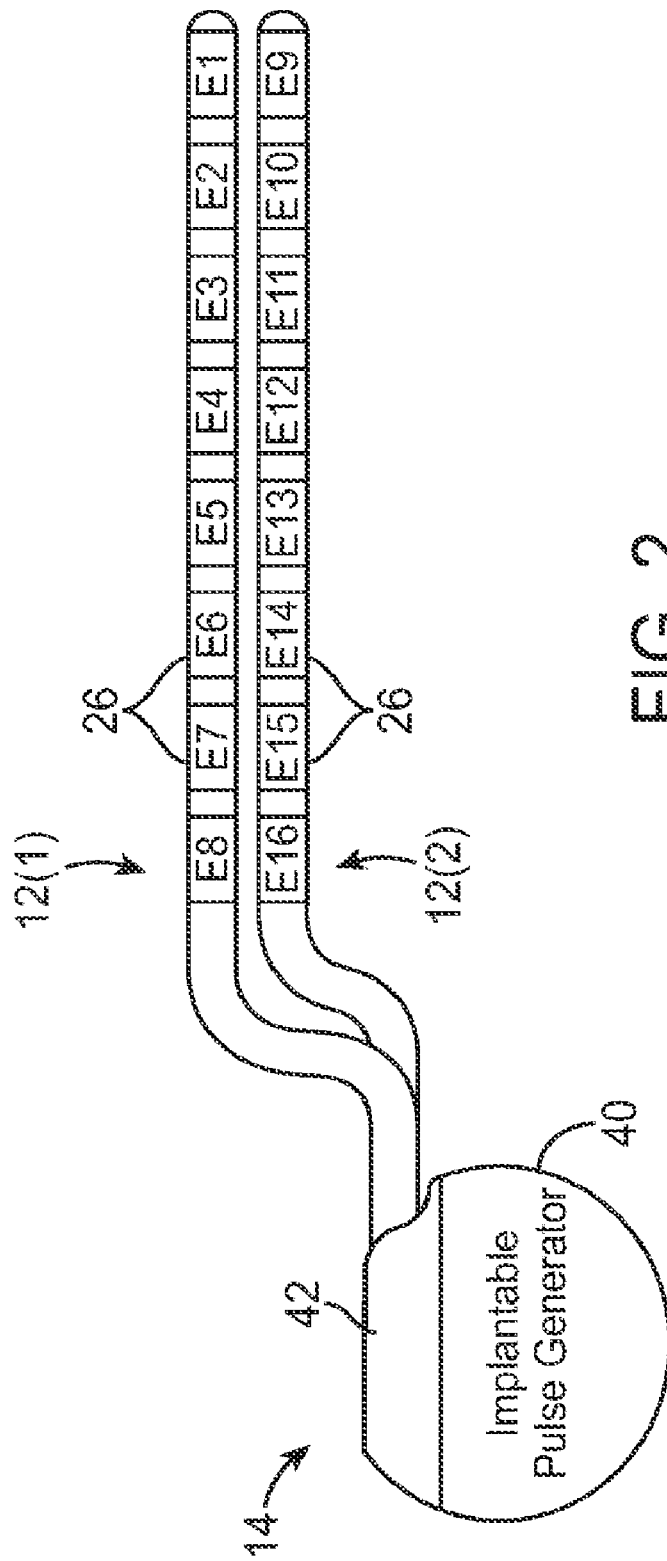
FIG. 2 is a side view of an implantable pulse generator and a pair of stimulation leads that can be used in the SCS system of FIG. 1.

Referring now to FIG. 2, the external features of the stimulation leads 12 and the IPG 14 will be briefly described. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the stimulation leads 12 mate in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 3:
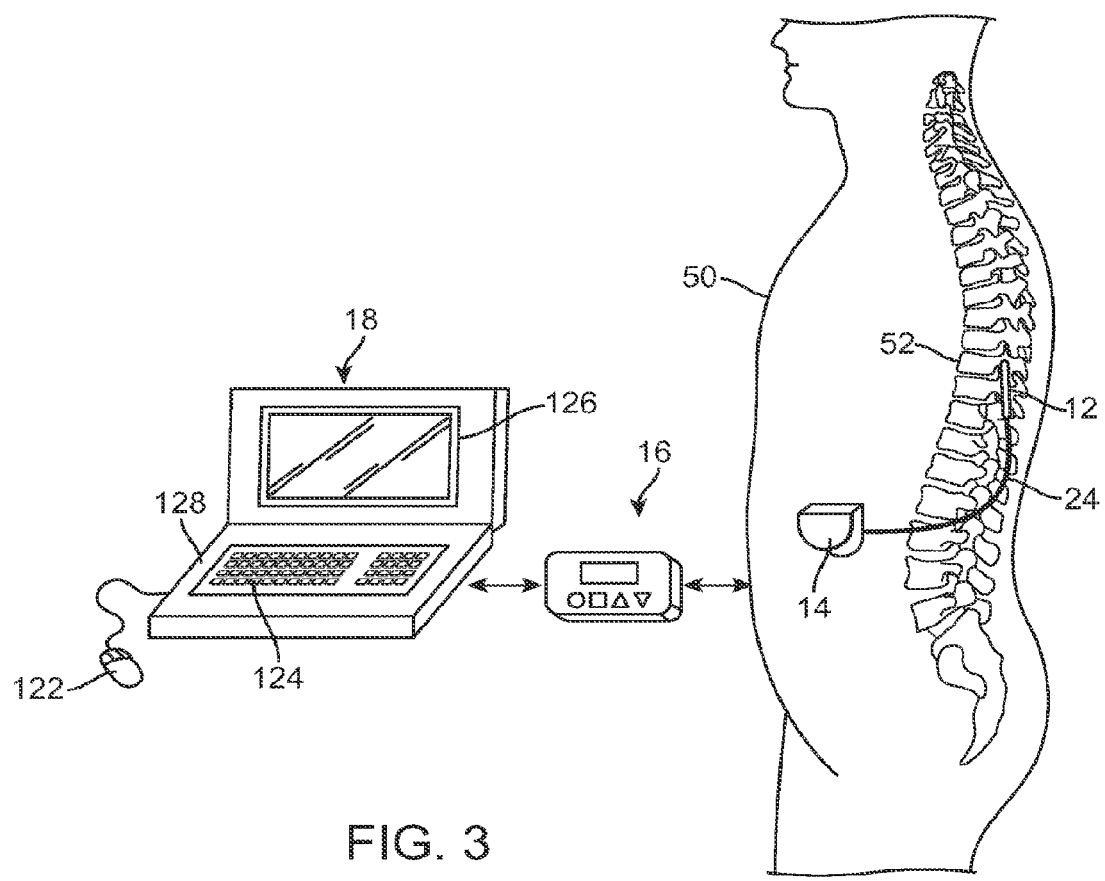
FIG. 3 is a plan view of the SCS system of FIG. 1 in use with a patient.

As shown in FIG. 3, the electrode leads 12 are implanted within the spinal column 52 of a patient 50. The preferred placement of the electrode leads 12 is adjacent, i.e., resting upon near, or upon the dura, adjacent to the spinal cord area to be stimulated. Due to the lack of space near the location where the electrode leads 12 exit the spinal column 52, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 4:
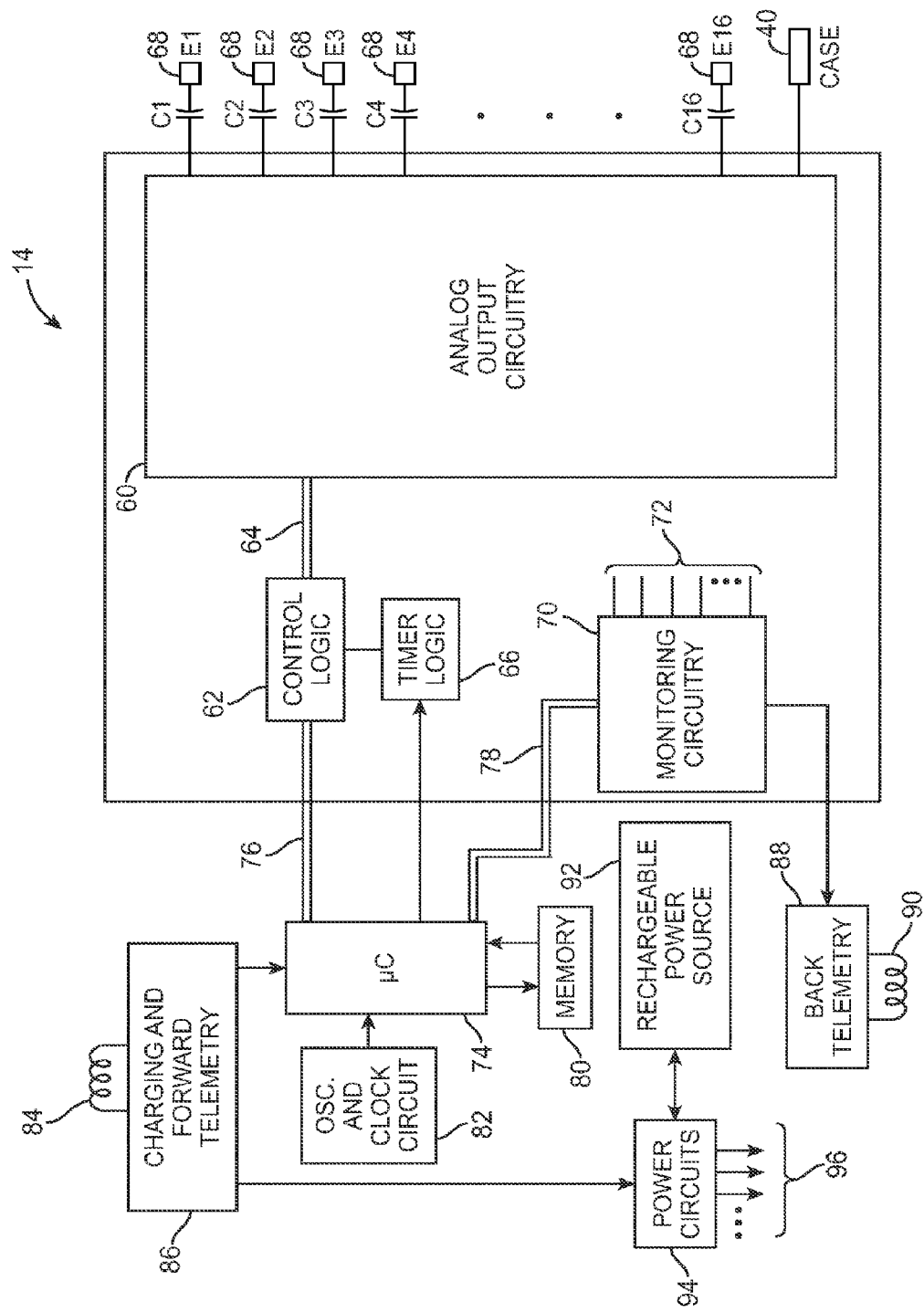
FIG. 4 is a block diagram of the internal componentry of the IPG of FIG. 2.

Turning next to FIG. 4, the main internal components of the IPG 14 will now be described. The IPG 14 includes stimulation output circuitry 60 configured for generating electrical stimulation energy in accordance with a defined pulsed waveform having a specified pulse amplitude, pulse rate, pulse width, and pulse shape under control of control logic 62 over data bus 64. Control of the pulse rate and pulse width of the electrical waveform is facilitated by timer logic circuitry 66, which may have a suitable resolution, e.g., 10 µs. The stimulation energy generated by the stimulation output circuitry 60 is output via capacitors C1-C16 to electrical terminals 68 corresponding to electrodes E1-E16.

The analog output circuitry 60 may either comprise independently controlled current sources for providing stimulation pulses of a specified and known amperage to or from the electrical terminals 68, or independently controlled voltage sources for providing stimulation pulses of a specified and known voltage at the electrical terminals 68 or to multiplexed current or voltage sources that are then connected to the electrical terminals 68. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993, 384, which are expressly incorporated herein by reference. The analog output circuitry 60 may also comprise pulse shaping circuitry (not shown) capable of shaping the pulses (e.g., a square pulse, an exponential pulse, a logarithmic pulse, a ramped pulse, a trapezoidal pulse, etc.). Further details discussing pulse shaping circuitry and the different pulse shapes that can be generated are disclosed in U.S. Patent Application Ser. No. 60/951,177, entitled "Use of Stimulation Pulse Shape to Control Neural Recruitment Order and Clinical Effect," which is expressly incorporated herein by reference.

The IPG 14 further comprises monitoring circuitry 70 for monitoring the status of various nodes or other points 72 throughout the IPG 14, e.g., power supply voltages, temperature, battery voltage, and the like. The monitoring circuitry 70 is also configured for measuring electrical parameter data (e.g., electrode impedance and/or electrode field potential). The IPG 14 further comprises processing circuitry in the form of a microcontroller (µC) 74 that controls the control logic 62 over data bus 76, and obtains status data from the monitoring circuitry 70 via data bus 78. The IPG 14 further comprises memory 80 and oscillator and clock circuit 82 coupled to the µC 74. The µC 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the µC 74 generates the necessary control and status signals, which allow the µC 74 to control the operation of the IPG 14 in accordance with a selected operating program and stimulation parameters. In controlling the operation of the IPG 14, the µC 74 is able to individually generate stimulus pulses at the electrical terminals 68 using the analog output circuitry 60, in combination with the control logic 62 and timer logic 66, thereby allowing each electrical terminal 68 to be paired or grouped with other electrical terminals 68, including the monopolar case electrode, to control the polarity, amplitude, rate, pulse width, pulse shape, and channel through which the current stimulus pulses are provided. The µC 74 facilitates the storage of electrical parameter data measured by the monitoring circuitry 70 within memory 80.

The IPG 14 further comprises a receiving coil 84 for receiving programming data (e.g., the operating program and/or stimulation parameters) from the external programmer (i.e., the RC 16 or CP 18) in an appropriate modulated carrier signal, and charging, and circuitry 86 for demodulating the carrier signal it receives through the receiving coil 84 to recover the programming data, which programming data is then stored within the memory 80, or within other memory elements (not shown) distributed throughout the IPG 14.

The IPG 14 further comprises back telemetry circuitry 88 and a transmission coil 90 for sending informational data to the external programmer. The back telemetry features of the IPG 14 also allow its status to be checked. For example, CP 18 initiates a programming session with the IPG 14, the capacity of the battery is telemetered, so that the CP 18 can calculate the estimated time to recharge. Any changes made to the current stimulus parameters are confirmed through back telemetry, thereby assuring that such changes have been correctly received and implemented within the implant system. Moreover, upon interrogation by the CP 18, all programmable settings stored within the IPG 14 may be uploaded to the CP 18.

The IPG 14 further comprises a rechargeable power source 92 and power circuits 94 for providing the operating power to the IPG 14. The rechargeable power source 92 may, e.g., comprise a lithium-ion or lithium-ion polymer battery or other form of rechargeable power. The rechargeable battery 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits, also known as "inverter circuits") received by the receiving coil 84.

To recharge the power source 92, the external charger 22 (shown in FIG. 1), which generates the AC magnetic field, is placed against, or otherwise adjacent, to the patient's skin over the implanted IPG 14. The AC magnetic field emitted by the external charger induces AC currents in the receiving coil 84. The charging and forward telemetry circuitry 86 rectifies the AC current to produce DC current, which is used to charge the power source 92. While the receiving coil 84 is described as being used for both wirelessly receiving communications (e.g., programming and control data) and charging energy from the external device, it should be appreciated that the receiving coil 84 can be arranged as a dedicated charging coil, while another coil, such as the coil 90, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference.

It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
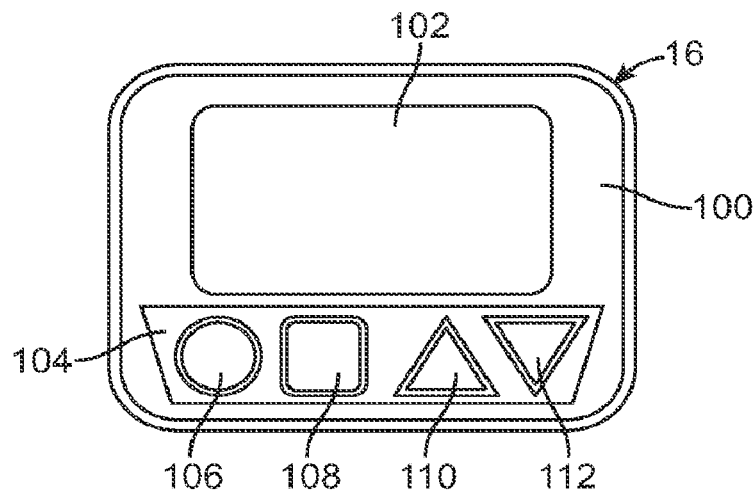
FIG. 5 is a plan view of a remote control that can be used in the SCS system of FIG. 1.

Referring now to FIG. 5, one exemplary embodiment of an RC 16 will now be described. As previously discussed, the RC 16 is capable of communicating with the IPG 14 or CP 18. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 140N and OFF. The button 108 serves as a select button that allows the RC 16 to switch between screen displays and/or parameters. The buttons 110 and 112 serve as up/down buttons that can actuated to increment or decrement any of stimulation parameters of the pulse generated by the IPG 14, including pulse amplitude, pulse width, and pulse rate. For example, the selection button 108 can be actuated to place the RC 16 in an "Pulse Amplitude Adjustment Mode," during which the pulse amplitude can be adjusted via the up/down buttons 110, 112, a "Pulse Width Adjustment Mode," during which the pulse width can be adjusted via the up/down buttons 110, 112, and a "Pulse Rate Adjustment Mode," during which the pulse rate can be adjusted via the up/down buttons 110, 112. Optionally, the RC 16 may be placed in a "Pulse Shaping Adjustment Mode," which is described in further detail in U.S. Patent Application Ser. No. 60/951,177, which was previously incorporated herein by reference.

Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 6:
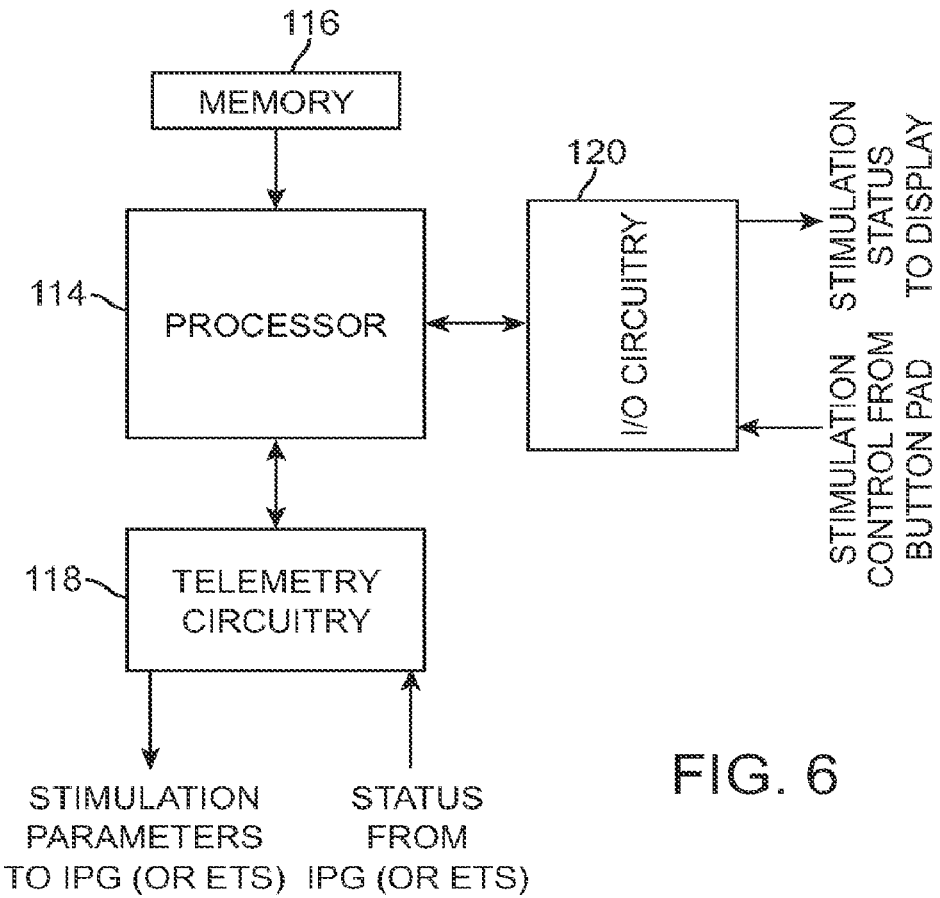
FIG. 6 is a block diagram of the internal componentry of the remote control of FIG. 5.

Referring to FIG. 6, the internal components of an exemplary RC 16 will now be described. The RC 16 generally includes a processor 114 (e.g., a microcontroller), memory 16 that stores an operating program for execution by the processor 114, as well as stimulation parameter sets in a look-up table (described below), input/output circuitry, and in particular, telemetry circuitry 118 for outputting stimulation parameters to the IPG 14 and receiving status information from the IPG 14, and input/output circuitry 120 for receiving stimulation control signals from the button pad 104 and transmitting status information to the display screen 102 (shown in FIG. 5). As well as controlling other functions of the RC 16, which will not be described herein for purposes of brevity, the processor 114 generates new stimulation parameter sets in response to the user operation of the button pad 104. These new stimulation parameter sets would then be transmitted to the IPG 14 via the telemetry circuitry 118. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 near the spinal cord.

As shown in FIG. 3, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18, under the control of the clinician, may actively control the characteristics of the electrical stimulation generated by the IPG 14 to allow the optimum stimulation parameters to be determined based on patient feedback and for subsequently programming the IPG 14 with the optimum stimulation parameters.

For example, the clinician may vary stimulation parameters, such as an electrode combination, which may involve turning on and off electrodes (e.g., turning off electrode E1 as an anode, and turning on electrode E2 as an off), or treating the electrode combinations as fractionalized electrode combinations, e.g., by gradually shifting current between anodic ones of the electrodes 26 and/or gradually shifting current between cathodic ones of the electrodes 26 (e.g., shifting anodic electrical current from electrode E1 to electrode E2 in 5% increments). Other stimulation parameters, such as the pulse amplitude, pulse width, and pulse rate, may also be controlled by the clinician.

Figure 7:
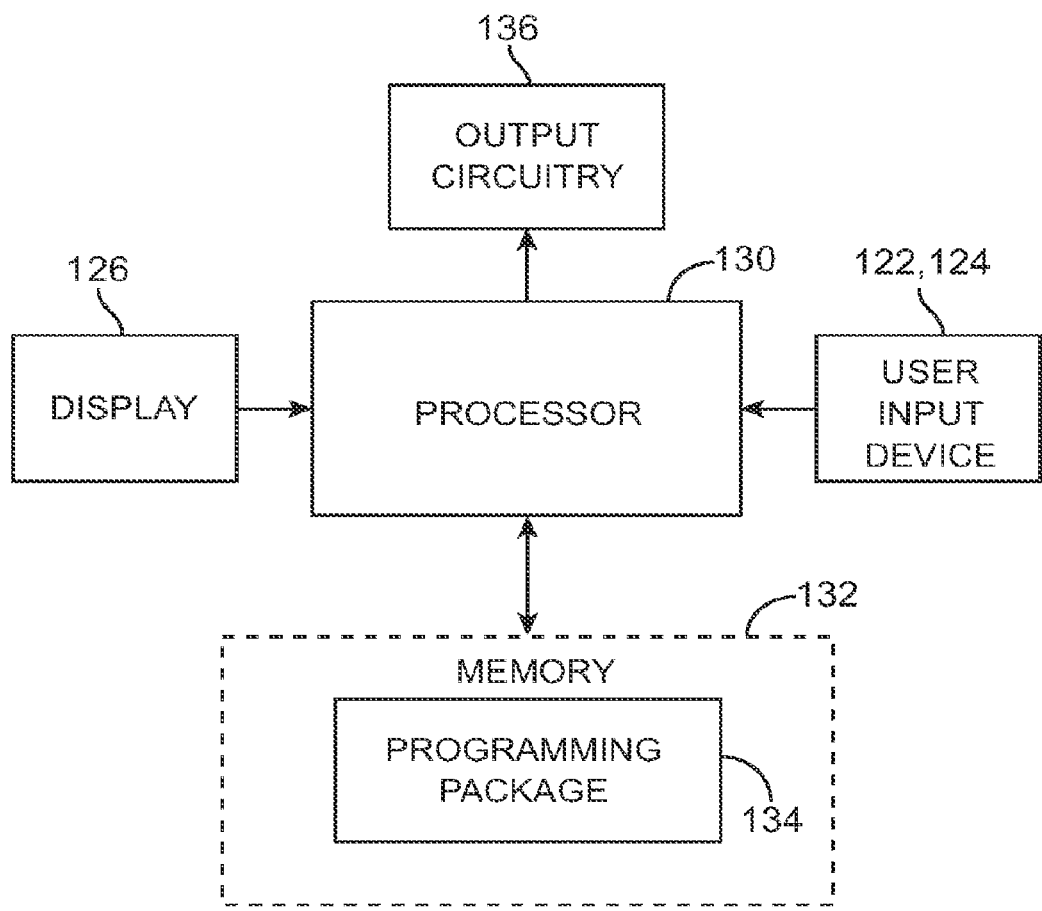
FIG. 7 is a block diagram of the components of a computerized programming system that can be used in the SCS system of FIG. 1.

To allow the clinician to perform these functions, the CP 18 includes a mouse 122, a keyboard 124, and a programming display screen 126 housed in a case 128. It is to be understood that in addition to, or in lieu of, the mouse 122, other directional programming devices may be used, such as a joystick, or directional keys included as part of the keys associated with the keyboard 124. As shown in FIG. 7, the CP 18 generally includes a processor 130 (e.g., a central processor unit (CPU)) and memory 132 that stores a stimulation programming package 134, which can be executed by the processor 130 to allow a clinician to program the IPG 14 and RC 16. The CP 18 further includes output circuitry 136 (e.g., via the telemetry circuitry of the RC 16) for downloading stimulation parameters to the IPG 14 and RC 16 and for uploading stimulation parameters already stored in the memory 116 of the RC 16, via the telemetry circuitry 118 of the RC 16.

Further details discussing an exemplary stimulation programming package is described in U.S. Provisional Patent Application Ser. No. 61/080,187, entitled "System and Method for Converting Tissue Stimulation Programs in a Format Usable by an Electrical Current Steering Navigator," which is expressly incorporated herein by reference.

Significant to the present inventions, the CP 18 is designed to avoid, reverse, and/or manage neurological accommodation of the spinal cord fibers.

In one technique that avoids neurological accommodation, the CP 18 automatically varies one or more stimulation parameters during a programming session. In particular, the clinician varies a first stimulation parameter, and the CP 18 automatically varies a second stimulation parameter. For example, the clinician may vary the electrode combination (fractionalized or otherwise) by operating the CP 18 in the manner described above, and the CP 18 may, in addition to varying the electrode combination in response to clinician control, automatically vary a different stimulation parameter (e.g., pulse amplitude, pulse width, pulse rate, and polarity).

For the purposes of this specification, a multiphasic pulse (e.g., a biphasic pulse) will be considered a single pulse. For example, a change in polarity of the stimulation energy includes the change of polarity between multiphasic pulses, but will not encompass a change in phase within a single multiphasic pulse. A change in pulse amplitude of the stimulation energy includes the change of amplitude between multiphasic pulses, but will not encompass the change in amplitude of the phases within a single multiphasic pulse. A change in pulse width of the stimulation energy includes the change of the total width of the multiphasic pulse, but will not encompass the change in width of the phases within a single multiphasic pulse.

The more variance that the stimulation parameter exhibits, the less the chance that neurons will neurologically accommodate to the stimulation. For example, the stimulation parameter may be varied pseudo-randomly (i.e., a process that appears random, but is not, and exhibits statistical randomness while being generated by an entirely deterministic causal process) or randomly. As the stimulation parameters are varied, a plurality of stimulation parameter sets are generated from them and transmitted to the IPG 14 via the RC 16, which outputs a pulsed electrical waveform between the electrodes 12 in accordance with the stimulation parameter sets to stimulate the spinal cord tissue.

As will be described in further detail below, the automatic variance of the second stimulation parameter by the CP 18 allows the spinal cord tissue to be stimulated without undergoing neurological accommodation that would otherwise occur if the second stimulation parameter were not varied. Based on the result of the spinal cord stimulation (e.g., using verbal feedback from the patient), the CP 18 can program the IPG 14 via the RC 16 with a new set of stimulation parameters, which can be stored within and subsequently used by the IPG 14 to output pulsed electrical waveforms to the electrodes 12 in a stand-alone mode (i.e., when not communicating with the RC 16 or CP 18). In the alternative case where an external controller is used with a receiver-stimulator, the external controller can be programmed with the new set of stimulation parameters, with the receiver-stimulator outputting the pulsed electrical waveform in accordance with this new stimulation parameter set.

Figure 8:
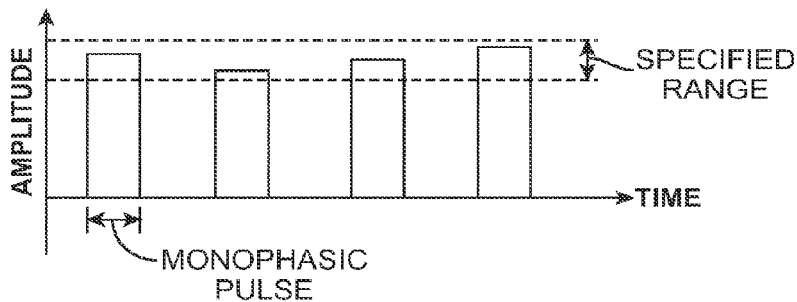
FIG. 8 is an exemplary mono-phasic pulsed electrical waveform that can be output by the IPG of FIG. 2 to prevent neurological accommodation of spinal cord tissue.
Figure 9:
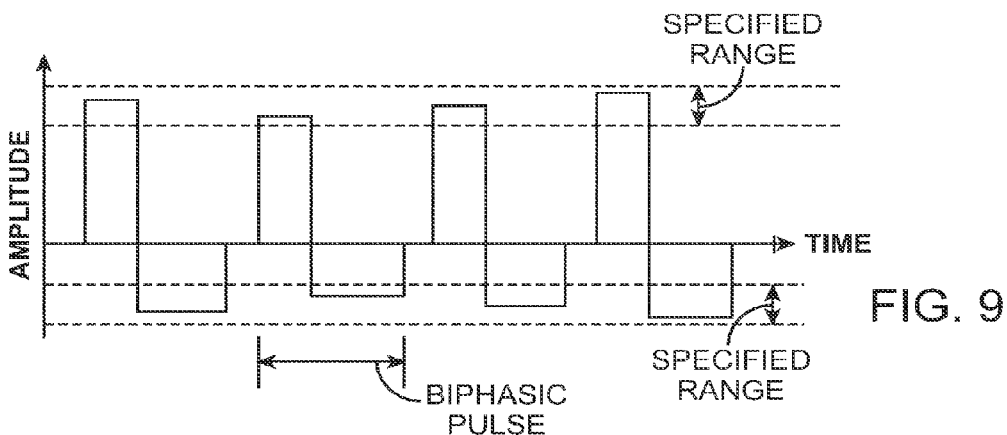
FIG. 9 is an exemplary bi-phasic pulsed electrical waveform that can be output by the IPG of FIG. 2 to prevent neurological accommodation of spinal cord tissue.

As one example, the CP 18 may automatically vary the pulse amplitude of the pulsed electrical waveform. As shown in FIG. 8, the amplitudes of monophasic pulses may be varied, and as shown in FIG. 9, the amplitudes of biphasic pulses may be varied. In the illustrated embodiment, the pulse amplitudes are varied within a specified amplitude range, with a single amplitude range being used to limit the anodic pulses of the monophasic pulsed waveform shown in FIG. 8, and two amplitude ranges being used to respectively limit the anodic pulses and cathodic pulses of the biphasic pulsed waveform shown in FIG. 9. To provide the best results with respect to preventing neurological accommodation, the pulse amplitudes are preferably varied in a manner that both increases and decreases the pulse amplitudes, as shown in FIGS. 8 and 9. For example, the pulse amplitudes may be pseudo-randomly or randomly varied.

Figure 10:
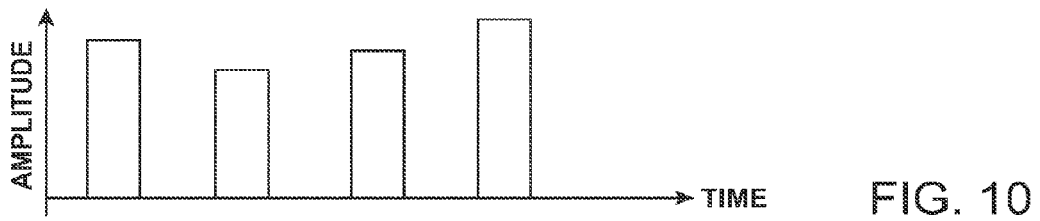
FIG. 10 is another exemplary mono-phasic pulsed electrical waveform that can be output by the IPG of FIG. 2 to prevent neurological accommodation of spinal cord tissue.
Figure 11:
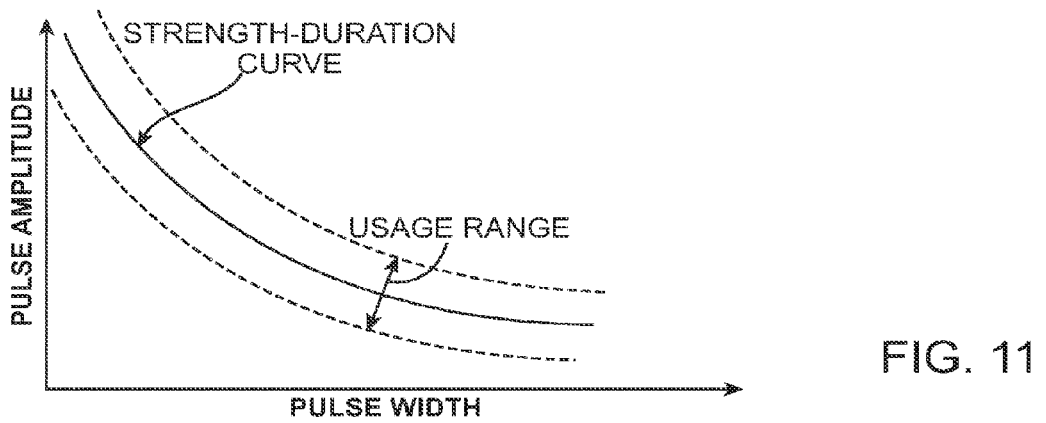
FIG. 11 is an exemplary plot of a strength-duration curve having a usage range in which the mono-phasic pulsed electrical waveform of FIG. 10 is maintained.

The CP 18 may also vary the pulse width of the pulsed electrical waveform, either separately or in addition to varying the pulse amplitude. For example, as shown in FIG. 10, the pulse amplitude and pulse width of each pulse are inversely varied relative to each other (i.e., as the pulse amplitude is increased, the pulse width is decreased, and as the pulse amplitude is decreased, the pulse width is increased). Preferably, if both the pulse width and pulse amplitude are varied, they are varied in such a way as to maintain each pulse within a specified percentage of the usage range of a strength-duration curve, as shown in FIG. 11.

Notably, a strength-duration curve represents the pulse amplitude and pulse width needed to stimulate a nerve fiber of a specified diameter, and the usage range with respect to the strength-duration curve is the variance from the strength-duration curve that maintains the stimulation energy between the point at which it is perceived by the patient and the point at which it is uncomfortable for the patient. As one example, the pulse amplitude and pulse width can be varied, so that the strength-duration of the stimulation energy is maintained within 80% of the usage range. Thus, in this case, if the pulse amplitude is varied (either non-randomly, pseudo-randomly, or randomly), the pulse width required to maintain the strength-duration of the stimulation energy within 80% of the usage range will be computed and used (either in a predetermined manner or dynamically), and if the pulse width is varied (either non-randomly, pseudo-randomly, or randomly), the pulse amplitude required to maintain the strength-duration of the stimulation energy within 80% of the usage range will be computed and used (either in a predetermined manner or dynamically).

Figure 12:
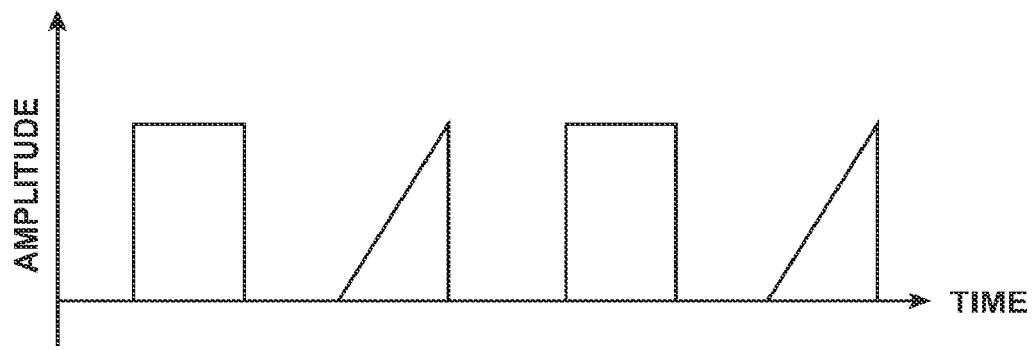
FIG. 12 is still another exemplary mono-phasic pulsed electrical waveform that can be output by the IPG of FIG. 2 to prevent neurological accommodation of spinal cord tissue.

As another example, the CP 18 may automatically vary the pulse shape of the pulsed electrical waveform. Such pulse shapes may include, e.g., a square pulse, a sinusoidal pulse, exponential pulse, logarithmic pulse, ramped pulse, triangle pulse, trapezoidal pulse, symmetrical biphasic pulse, asymmetrical biphasic pulse, etc. As shown in FIG. 12, the pulse shape of the pulsed electrical waveform is varied by alternating between a series of square pulses and a series of ramp pulses. Further details on the use of different pulse shapes are described in U.S. Patent Application Ser. No. 60/951,177, which was previously incorporated herein by reference.

As still another example, the CP 18 may automatically burst stimulation on and off, thereby preventing the target nerve fibers from developing neurological accommodation, since the time that the pulsed electrical waveform is on will only be a percentage of the length of the programming session. The burst rate may range anywhere from several times a second to several times an hour. In addition, because patients tend to notice abrupt changes more easily than gradual changes, the bursting of the stimulation will allow the patient to better localize where the paresthesia is located and better determine the intensity of the paresthesia.

As yet another example, the CP 18 may automatically vary the electrode combinations, so that the same nerve fibers are not being constantly stimulated. In this case, the CP 18 preferably selects the electrode combinations in a manner that significantly varies the locus of the stimulation field from one electrode combination to the next electrode combination. For example, the CP 18 may automatically switch the cathodic current from electrode E1 to electrode E8, then from electrode E8 to electrode E2, then from electrode E2 to electrode E7, then from electrode E7 to electrode E3, then from electrode E3 to electrode E6, then from electrode E6 to electrode E4, and then from electrode E4 to electrode E5. This should be contrasted with the normal variance of electrode combinations, which more gradually varies the locus of stimulation (e.g., from electrode E1 to electrode E2, than from electrode E2 to electrode E3, then from electrode E4 to electrode E5, and so forth), and therefore, is more apt to promote neurological accommodation. If two leads are used, the CP 18 may automatically switch the cathodic current back and forth between the two leads as well to provide even more variance of the stimulation loci from one electrode combination to the next.

Between the automatic switching of electrode combinations, the clinician may gradually shift cathodic current (i.e., "steer") between the present cathode and the surrounding electrodes or the CP 18 may automatically perform this current steering function. Because the clinician may not have a logical picture of the fractionalized electrode configurations that provide the best paresthesia due to the automatic "jumping" of the cathode from one electrode to the next, the CP 18 may generate a map of which electrode combinations (fractionalized or otherwise) had the best effects on paresthesia.

As an aside, the locus of the stimulation field can be varied (e.g., by varying the electrode combination or fractionalized electrode combination) outside of the programming context to prevent neurological accommodation during therapeutic use. In particular, the IPG 14 may be programmed to switch back and forth between different electrode combinations or fractionalized electrode combination) in order to displace the stimulation field between multiple locations, thereby stimulating different bundles of nerve fibers, while maintaining the same therapeutic effect (e.g., the same physical location on the patient, such as pain in the lower back, is treated). In this manner, the nerve fibers do not neurologically accommodate to the stimulation. Because the same therapeutic effect is maintained between the different loci of the stimulation fields, the patient will not readily discern when the IPG 14 switches between the different electrode combinations or fractionalized electrode combinations.

The CP 18 may include an optional "Yes" or "No" toggle switch (not shown) that allows the clinician to turn the above-described neurological accommodation avoidance features on and off. For example, if the clinician anticipates that an IPG for a patient can be programmed in a relatively short period of time, such that neurological accommodation is not likely, the clinician may turn the neurological accommodation avoidance feature off via operation of the toggle switch. In contrast, if the clinician anticipates that an IPG for the patient will need a relatively long period of time to be programmed, such that neurological accommodation is likely, the clinician may turn the neurological accommodation avoidance feature on via operation of the toggle switch.

Oftentimes, neurological accommodation cannot be avoided. However, in some of these cases, neurological accommodation can be reversed. In one technique that reverses neurological accommodation, the CP 18, during a programming session, prompts the IPG 14 to output a pulsed electrical waveform between the electrodes 12 while at least one selected electrode 12 has a first polarity (e.g., negative polarity), thereby stimulating the spinal cord tissue adjacent the selected electrode(s) 12.

When the spinal cord tissue undergoes neurological accommodation in response to the pulsed electrical waveform output between the electrodes 12 (e.g., based on a predetermined elapsed time), the CP 18 switches the selected electrode(s) 12 from the first polarity to a second polarity (e.g., positive polarity), and prompts the IPG 14 to output the pulsed electrical waveform between the electrodes 12 while the selected electrode(s) 12 have the second polarity, thereby hyperpolarizing the spinal cord tissue (and reversing the neurological accommodation). For example, the selected electrode(s) 12 may be operated in the first polarity a predetermined number of pulses (e.g., in the range of 10-1000 pulses), and then operated in the second polarity a predetermined number of pulses (e.g., in the range of 10-1000 pulses).

The CP 18 then switches the selected electrode(s) 12 from the second polarity back to the first polarity, and prompts the IPG 14 to output the pulsed electrical waveform between the electrodes 12 while the selected electrode(s) 12 have the first polarity, thereby stimulating the previously hyperpolarized neural tissue (i.e., the neural tissue is depolarized).

When the selected electrode(s) 12 are in the first polarity, the pulsed electrical waveform may be output between the electrodes in accordance with a set of stimulation parameters (e.g., any of those previously described above), in which case, one or more these stimulation parameters can be varied by the clinician as the pulsed electrical waveform is output between the electrodes. The IPG 14 may be programmed with a new set of stimulation parameters based on the result of the spinal cord stimulation.

Preferably, to prevent any undesirable side effects, the amplitude of the pulsed electrical waveform output when the selected electrode(s) 12 have the first polarity is less than (e.g., one-third) the amplitude of the pulsed electrical waveform output when the selected electrode(s) 12 have the second polarity. Switching between the polarities may be initiated either manually by the clinician or automatically by the CP 18.

Oftentimes, neurological accommodation can neither be avoided nor reversed. In these cases, the CP 18 may manage the effects of the neurological accommodation during the programming process.

In one technique for managing the effects of neurological accommodation, the clinician varies an electrode combination (fractionalized or otherwise) while the pulse rate or pulse width is fixed. For example, the clinician may use the CP 18 to vary the electrode combination, while the CP 18 automatically fixes the pulse rate or pulse width. The CP 18 then generates a plurality of stimulation parameter sets from the different electrode combinations and the fixed pulse rate or pulse width, and prompts the IPG 14 to output a pulsed electrical waveform between the electrodes 12 in accordance with these stimulation parameter sets, such that paresthesia is achieved while allowing the spinal cord tissue to undergo neurological accommodation.

The CP 18 then automatically changes the pulse rate or pulse width, and then fixes the changed pulse rate or pulse width while the electrode combination is varied again by the clinician. The CP 18 then generates another plurality of stimulation parameter sets from the different electrode combinations and the fixed pulse rate or pulse width, and prompts the IPG 14 to output a pulsed electrical waveform between the electrodes 12 in accordance with these other stimulation parameter sets, such that the paresthesia is maintained while the spinal cord tissue is still neurologically accommodated. Notably, without the change in the pulse rate or pulse width, paresthesia may be lost due to the neurological accommodation of the spinal cord tissue. Changing the pulse rate may cause the spinal cord tissue to respond differently, because some stimulus information is encoded at time between the pulses. Large changes in pulse rate may be more effective than smaller incremental changes in rate over time. Pulse rate has the virtue of affecting the perceived intensity of the stimulation less than other stimulation parameters. Ultimately, the CP 18 may then be operated to program the IPG 14 with a new set of stimulation parameters based on the result of the spinal cord stimulation.

Figure 13:
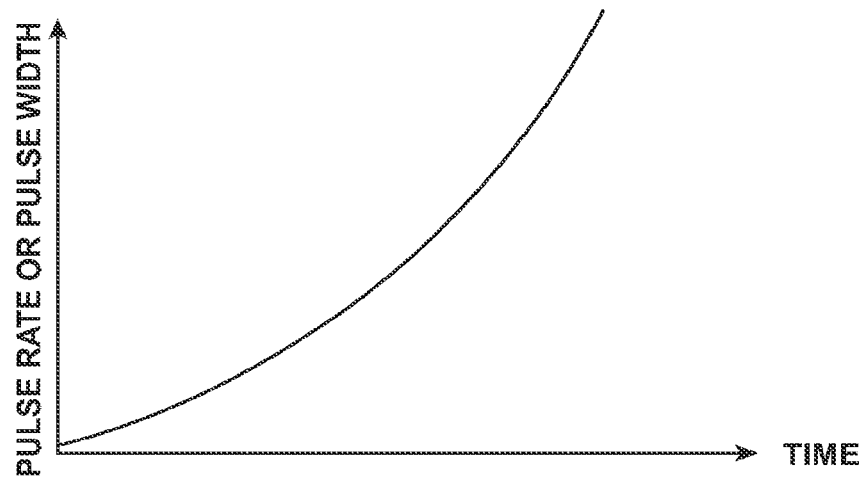
FIG. 13 is a predetermined pulse rate or pulse width curve that can be used to output a pulse electrical waveform from the IPG of FIG. 2 to manage neurological accommodation of the spinal cord tissue.

The pulse rate or pulse rate can be changed in accordance with a predetermined curve (as shown in FIG. 13), which can be generated, e.g., based on data collected from patients that have previously undergone neurological accommodation or on data collected from the current patient.

Figure 14:
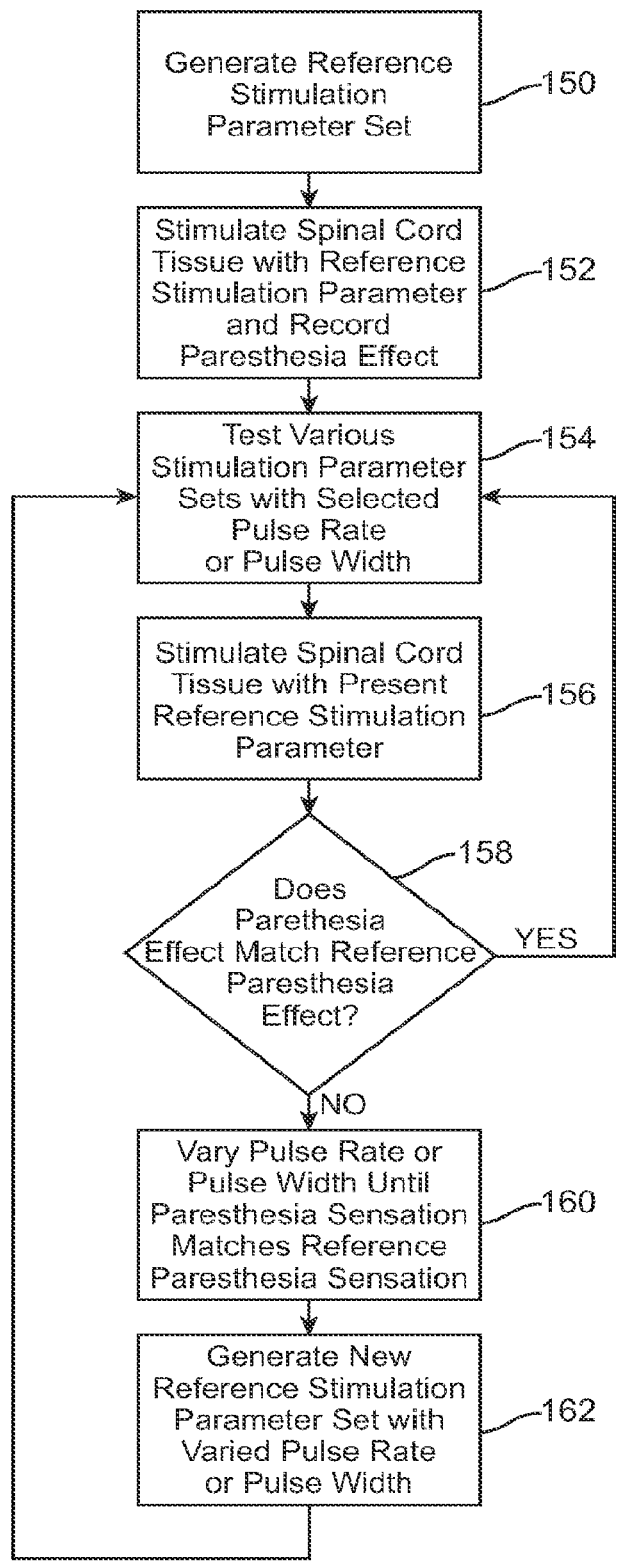
FIG. 14 is a flow diagram of a method used to manage neurological accommodation of the spinal cord tissue.

Referring to FIG. 14, if data is to be collected from the current patient, the CP 18, at the beginning of the programming session, can generate a reference set of stimulation parameters from a first reference stimulation of the same type as the stimulation parameter varied by the clinician (in this case, a reference electrode combination) and a second stimulation parameter of the same type as the stimulation parameter changed by the CP 18 (in this case, a reference pulse rate or pulse width) (step 150). Prior to allowing the spinal cord tissue to undergo neurological accommodation (preferably, at the beginning of the programming process), the CP 18 prompts the IPG 14 to output the pulsed electrical waveform between the electrodes 12 in accordance with the reference stimulation parameter set (in this case, a reference electrode combination and a reference pulse rate or pulse width), thereby stimulating the spinal cord tissue to provide a paresthesia sensation that can then be remembered by the patient and recorded (step 152).

Throughout the programming process when various stimulation parameter sets (with the currently selected pulse rate or pulse width) are tested by the clinician (step 154), the CP 18 or clinician may then periodically return to this reference stimulation parameter set by prompting the IPG 14 to output the pulsed electrical waveform between the electrodes 12 in accordance with the reference stimulation parameter set (step 156). If the spinal cord tissue has undergone neurological accommodation, thereby changing the reference therapeutic effect (in this case, if the paresthesia sensation is no longer felt or reduced) originally obtained at the beginning of the programming process (step 158), the CP 18 determines the pulse rate or pulse width needed to get the reference paresthesia sensation back by varying the pulse rate or pulse width until the current paresthesia sensation matches the reference paresthesia sensation (using feedback from the patient) (step 160). A new reference stimulation parameter set can then be generated using this varied pulse rate or pulse width (step 162). This varied pulse rate or pulse width is then used during the programming process (testing various stimulation parameter sets) until the CP 18 (step 154) returns to the new reference stimulation parameter set and a new pulse rate or pulse width is determined (step 164). If, at step 158, the spinal cord tissue has not undergone neurological accommodation, thereby not changing the reference therapeutic effect (in this case, the paresthesia sensation feels the same), the pulse rate or pulse width is not changed, and thus, the current pulse rate or pulse width is used during the programming process (testing various stimulation parameter sets) until the CP 18 returns to the new reference stimulation parameter set and a new pulse rate or pulse width is determined (step 164).

Ultimately, the CP 18 may then be operated to program the IPG 14 with a new set of stimulation parameters based on the result of the spinal cord stimulation.

Figure 15:
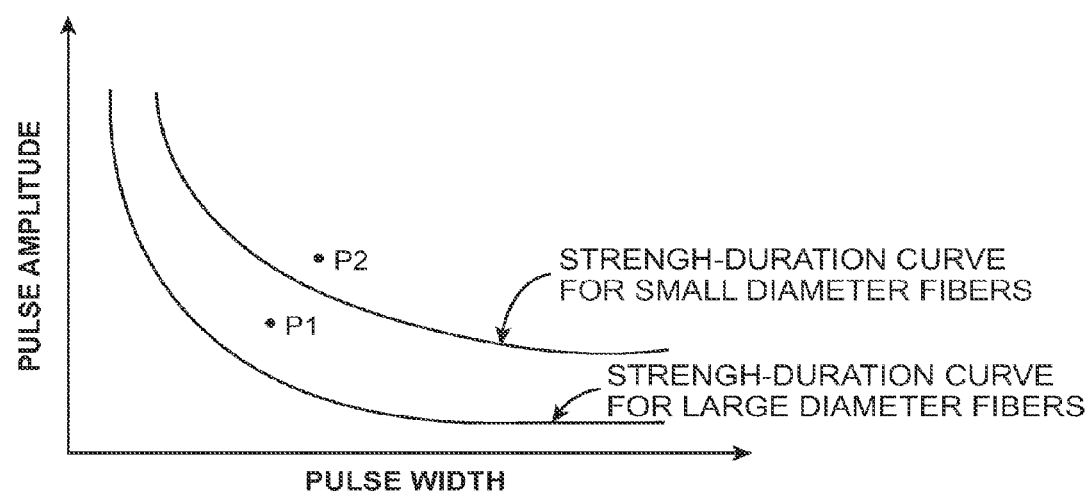
FIG. 15 is an exemplary plot of two strength-duration curves for respective small diameter fibers and large diameter fibers that can be used to manage neurological accommodation of the spinal cord tissue.

In another technique for managing the effects of neurological accommodation during the programming process, the CP 18 prompts the IPG 14 to output a pulsed electrical waveform between the electrodes 12 in accordance with a specified pulse amplitude and a specified pulse width. The CP 18 maintains the pulsed electrical waveform between a first strength-duration curve for relatively large diameter spinal cord fibers and a second strength-duration curve for relatively small diameter spinal cord fibers, such that the large diameter fibers are stimulated and the small diameter fibers are not stimulated. For example, as shown in FIG. 15, the pulse amplitude and pulse width can be selected, such that the pulsed electrical waveform is maintained at point P1.

The large diameter fibers can then be allowed to neurologically accommodate, and after a predetermine period of time (e.g., 10 minutes), the CP 18 can then automatically increase one or both of the specified amplitude and the specified pulse width, such that the pulsed electrical waveform is on or above the second strength-duration curve, thereby stimulating the small diameter fibers. For example, as shown in FIG. 15, the pulse amplitude and pulse width can be selected, such that the pulsed electrical waveform is maintained at point P2. Thus, it can be appreciated that there are least some neurons in the target spinal cord tissue that have not yet neurologically accommodated during this process. Ultimately, the CP 18 may then be operated to program the IPG 14 with a new set of stimulation parameters based on the result of the spinal cord stimulation.

In another technique for managing the effects of neurological accommodation, the CP 18, at the beginning of the programming process, prompts the IPG 14 to output a pulsed electrical waveform between the electrodes 12, such that the spinal cord tissue is stimulated and undergoes neurological accommodation. Preferably, the pulsed electrical waveform is initially output with the highest pulse amplitude tolerable for the patient. The CP 18 then decreases the pulse amplitude of the pulsed electrical waveform, generates a plurality of stimulation parameter sets having the decreased amplitude, and again prompts the IPG 14 to output the pulsed electrical waveform with the decreased pulse amplitude between the electrodes 12 in accordance with the stimulation parameter sets, such that the neural tissue is stimulated and remains neurologically accommodated. Ultimately, the CP 18 may then be operated to program the IPG 14 with a new set of stimulation parameters based on the result of the spinal cord stimulation.

It should be appreciated that because the targeted areas of the spinal cord tissue are neurologically accommodated throughout the entire programming process (i.e., the targeted areas are preconditioned to be neurologically accommodated), the sensation of paresthesia achieved during the neurological accommodation is not lost during the programming process.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of operating a neurostimulation device, comprising:
varying a first stimulation parameter under user control while fixing a second stimulation parameter;
generating a plurality of stimulation parameter sets from the varied first stimulation parameter and the fixed second stimulation parameter;
outputting a pulsed electrical waveform from the neurostimulation device between a plurality of electrodes in accordance with the plurality of stimulation parameter sets, such that a therapeutic effect is achieved while allowing neural tissue to undergo neurological accommodation;
changing the second stimulation parameter;
varying the first stimulation parameter under user control while fixing the second changed stimulation parameter;
generating another plurality of stimulation parameter sets from the varied first stimulation parameter and the fixed changed second stimulation parameter;
outputting the pulsed electrical waveform from the neurostimulation device between the plurality of electrodes in accordance with the other plurality of stimulation parameter sets to maintain the therapeutic effect while the neural tissue is neurologically accommodated.

2. The method of claim 1, further comprising programming the neurostimulation device with a new set of stimulation parameters based on a result of the therapeutic effect.

3. The method of claim 1, wherein the first stimulation parameter is an electrode combination.

4. The method of claim 1, wherein the first stimulation parameter is a fractionalized electrode combination.

5. The method of claim 4, wherein the fractionalized electrode combination is varied by gradually shifting current between anodic ones of the electrodes or gradually shifting current between cathodic ones of the electrodes.

6. The method of claim 1, wherein the second stimulation parameter is automatically changed.

7. The method of claim 1, wherein the second stimulation parameter is a pulse rate.

8. The method of claim 1, wherein the second stimulation parameter is a pulse width.

9. The method of claim 1, wherein the second stimulation parameter is changed in accordance with a predetermined curve.

10. The method of claim 9, further comprising generating the predetermined curve based on data collected from patients that have undergone neurological accommodation.

11. The method of claim 9, further comprising:
generating a reference set of stimulation parameters from a first reference stimulation parameter of the same type as the first stimulation parameter, and a second stimulation parameter of the same type as the second stimulation parameter;
prior to allowing the neural tissue to undergo neurological accommodation, outputting the pulsed electrical waveform from the neurostimulation device between the electrodes in accordance with the reference stimulation parameter set, thereby stimulating the neural tissue to provide a reference therapeutic effect; and
after allowing the neural tissue to undergo neurological accommodation, outputting the pulsed electrical waveform from the neurostimulation device between the electrodes in accordance with the reference stimulation parameter set, thereby providing an effect different from the reference therapeutic effect, and varying the second reference stimulation parameter until the effect matches the reference therapeutic effect, wherein the varied second reference stimulation parameter is used as the changed second stimulation parameter.

12. The method of claim 1, wherein the neural tissue is spinal cord tissue, and the therapeutic effect is pain relief.

13. A method of operating a neurostimulation device, comprising:
outputting a pulsed electrical waveform from the neurostimulation device between a plurality of electrodes in accordance with a specified pulse amplitude and a specified pulse width;
maintaining the pulsed electrical waveform between a first strength-duration curve for relatively large fibers of neural tissue and a second strength-duration curve for relatively small fibers of the neural tissue, whereby the relatively large fibers are stimulated and the relatively small fibers are not stimulated;
allowing the relatively large fibers of the neural tissue to neurological accommodate when the pulsed electrical waveform is between the first and second strength-duration curves; and
increasing one or both of the specified amplitude and the specified pulse width, such that the pulsed electrical waveform is on or above the second strength-duration curve, whereby the relatively small fibers are stimulated.

14. The method of claim 13, further comprising programming the neurostimulation device with a new set of stimulation parameters based on a result of the neural stimulation.

15. The method of claim 13, wherein the specified amplitude is increased.

16. The method of claim 13, wherein the specified pulse width is increased.

17. The method of claim 13, wherein the one or both of the specified amplitude and the specified pulse width is automatically increased.

18. The method of claim 13, wherein the one or both of the specified amplitude and the specified pulse width is increased at a predetermined period of time after the pulsed electrical waveform is initially output by the neurostimulation device.

19. The method of claim 13, wherein the neural tissue is spinal cord tissue.

20. The method of claim 13, further comprising varying a stimulation parameter under user control.

21. The method of claim 20, wherein the stimulation parameter is an electrode combination.

22. The method of claim 20, wherein the first stimulation parameter is a fractionalized electrode combination.

23. The method of claim 22, wherein the fractionalized electrode combination is varied by gradually shifting current between anodic ones of the electrodes or gradually shifting current between cathodic ones of the electrodes.

24. A method of programming a neurostimulation device, comprising:
initially outputting a pulsed electrical waveform from the neurostimulation device between a plurality of electrodes, such that neural tissue of a patient is stimulated and undergoes neurological accommodation;
decreasing a pulse amplitude of the pulsed electrical waveform;
generating a plurality of stimulation parameter sets having the decreased amplitude;
outputting the pulsed electrical waveform with the decreased pulse amplitude in accordance with the stimulation parameter sets, such that the neural tissue is stimulated and remains neurologically accommodated; and
programming the neurostimulation device with a new set of stimulation parameters based on a result of the neural tissue stimulation.

25. The method of claim 24, wherein the pulsed electrical waveform is initially output with the highest pulse amplitude tolerable for the patient.

26. The method of claim 24, wherein the neural tissue is spinal cord tissue.

27. The method of claim 24, further comprising varying a stimulation parameter under user control, wherein the plurality of stimulation parameter sets are generated from the varied stimulation parameter.

28. The method of claim 24, wherein the stimulation parameter is an electrode combination.

29. The method of claim 24, wherein the first stimulation parameter is a fractionalized electrode combination.

30. The method of claim 29, wherein the fractionalized electrode combination is varied by gradually shifting current between anodic ones of the electrodes or gradually shifting current between cathodic ones of the electrodes.

* * * * *